US007846713B2

(12) United States Patent
Lamont et al.

(10) Patent No.: US 7,846,713 B2
(45) Date of Patent: Dec. 7, 2010

(54) CALIBRATING MICROARRAYS

(75) Inventors: John Victor Lamont, Co. Antrim (GB); Robert Ivan McConnell, Co. Antrim (GB); Stephen Peter Fitzgerald, Co. Antrim (GB); Maria Luz Rodriguez, Co. Antrim (GB)

(73) Assignee: Randox Laboratories Ltd., Northern Ireland (GB)

( * ) Notice: Subject to any disclaimer, the term of this patent is extended or adjusted under 35 U.S.C. 154(b) by 276 days.

(21) Appl. No.: 10/491,811

(22) PCT Filed: Oct. 10, 2002

(86) PCT No.: PCT/GB02/04593
§ 371 (c)(1),
(2), (4) Date: Jul. 14, 2004

(87) PCT Pub. No.: WO03/031976

PCT Pub. Date: Apr. 17, 2003

(65) Prior Publication Data
US 2004/0241700 A1 Dec. 2, 2004

(30) Foreign Application Priority Data
Oct. 10, 2001 (GB) ................ 0124338.5

(51) Int. Cl.
*C12M 1/00* (2006.01)
(52) U.S. Cl. ............ 435/283.1; 435/7.1; 435/287.1; 435/287.2; 435/288.3; 435/288.4; 435/288.7; 436/518; 436/164; 436/807; 436/809
(58) Field of Classification Search ............ 422/50, 422/52, 61, 68.1, 82.05, 82.08; 435/4, 7.1, 435/7.92, 7.94, 174, 175, 176, 177, 283.1, 435/287.1, 288.4, 288.7, 287.2, 288.3; 436/8, 436/10, 15, 164, 172, 518, 807, 809
See application file for complete search history.

(56) References Cited
U.S. PATENT DOCUMENTS

| 4,459,360 | A |   | 7/1984  | Marinkovich |
| 5,554,339 | A | * | 9/1996  | Cozzette et al. ............ 422/50 |
| 5,599,668 | A | * | 2/1997  | Stimpson et al. ............ 435/6 |
| 5,677,196 | A | * | 10/1997 | Herron et al. ............ 436/518 |
| 5,726,064 | A | * | 3/1998  | Robinson et al. .......... 436/514 |
| 5,968,515 | A | * | 10/1999 | Thacker .................. 424/193.1 |
| 6,066,448 | A | * | 5/2000  | Wohlstadter et al. ........ 435/6 |
| 6,110,749 | A | * | 8/2000  | Obremski et al. .......... 436/527 |
| 6,232,066 | B1 | * | 5/2001 | Felder et al. ................ 435/6 |
| 6,232,608 | B1 | * | 5/2001 | Giebeler et al. .......... 250/458.1 |
| 6,341,182 | B1 | * | 1/2002 | Fitzgerald et al. .......... 382/273 |
| 6,815,217 | B2 | * | 11/2004| Karl et al. .................. 436/518 |
| 6,916,621 | B2 | * | 7/2005 | Shah ............................ 435/6 |
| 2002/0015958 | A1 | * | 2/2002 | Audeh et al. .................. 435/6 |
| 2002/0058273 | A1 | * | 5/2002 | Shipwash ...................... 435/6 |
| 2002/0168692 | A1 | * | 11/2002 | Cass ........................ 435/7.9 |
| 2003/0012695 | A1 | * | 1/2003 | Shalon et al. ............ 422/68.1 |
| 2003/0148542 | A1 | * | 8/2003 | Pawlak et al. .............. 436/518 |
| 2003/0153013 | A1 | * | 8/2003 | Huang ........................ 435/7.9 |

FOREIGN PATENT DOCUMENTS

| GB | 2 324 866 A | 11/1998 |
| WO | WO 97/46313 | 12/1997 |
| WO | WO 99/13313 | 3/1999 |
| WO | WO 01/09607 A1 | 2/2001 |
| WO | WO 01/20330 A1 | 3/2001 |
| WO | WO 01/92870 A2 | 6/2001 |

* cited by examiner

*Primary Examiner*—Melanie J Yu
(74) *Attorney, Agent, or Firm*—Oliff & Berridge, PLC

(57) ABSTRACT

An assay for measuring the amount of a first analyte in a sample, comprises the steps of: (i) contacting the sample with a device that comprises one or more first reaction sites which comprise a first ligand having affinity for the first analyte, and a series of second reaction sites each comprising different known concentrations of an immobilized second analyte; (ii) removing any unbound first analyte; (iii) contacting the device with a second ligand that is detectably labelled and which has affinity for the first analyte, and a third ligand that is detectably labelled and which has affinity for the second analyte; (iv) removing any unbound second and third ligands; and (v) measuring the amount of second and third ligands, wherein measurement of the third ligand is used to establish a calibration curve, used to determine the amount of first analyte present in sample.

2 Claims, 4 Drawing Sheets

CALIBRATING MICROARRAYS

FIELD OF THE INVENTION

The present invention relates to improving the performance of microarrays in diagnostic assays, in particular for microarrays used in quantitive immunoassays.

BACKGROUND OF THE INVENTION

Immunoassays are ligand binding assays where the specific recognition of an antibody to the specific binding site of an analyte is exploited. The immunoassays usually involve the immobilisation of a ligand (antibody, other protein, hapten etc.) to a solid phase (support material) that will, in turn, be recognised by the analyte to be determined. The use of specific labelled detecting agents allows the subsequent detection and quantitation of the analyte in an aqueous sample. The amount of analyte present in the sample is a function of the bound labelled detecting agent: inversely proportional in competitive assays and directly proportional in noncompetitive assays.

Different immunoassays have been reported in which the solid phase that contains the ligands are plastic tubes (U.S. Pat. No. 3,646,346), discs (J. Lab. and Clin. Med., 70: 820, 1967), porous supports (U.S. Pat. No. 4,708,932, U.S. Pat. No. 4,459,360) and beads (Clin Chem. 37: 1521, 1991). The quantitation of analyte in these systems is carried out by the construction of individual external calibration curves; the concentration of each analyte being in a separate solid phase unit. These calibration curves may be stored and used to control runs of samples in which a particular analyte has to be measured.

There is now a growing awareness of the advantages of carrying out multianalyte determination on microarray-based technologies. These systems present greater flexibility and versatility with high throughput and sensitivity. Multiple ligands can be disposed on the surface of the support, each one defining individual discrete test regions (DTRs) of defined small volumes (pl or nl), permitting the simultaneous multiplexed detection and quantitation of multiple analytes in one sample. The amount of sample required per assay is also greatly reduced.

GB-A-2324866 discloses suitable microarrays that may be used in an immunoassay.

SUMMARY OF THE INVENTION

The present invention is based on the realisation that an internal calibration system can be used as part of a microarray to improve the accuracy of the detection system. The internal calibration system enables the calibration of an assay to be performed within one microarray while at the same time determining the unknown concentration of a target analyte in a sample.

According to a first aspect of the invention, a support material comprises an array of discrete first reaction sites, each reaction site comprising an immobilised first analyte, or a molecule that has affinity for the first analyte, and a series of second reaction sites with different known concentrations of a second analyte.

The series of reaction sites of different known concentrations allows a calibration curve to be established, which can be used to quantify the reaction occurring on the first reaction sites.

According to a second aspect of the invention, an assay for measuring the amount of a first analyte in a sample comprises the steps of:

(i) contacting the sample with a device that comprises one or more first reaction sites which comprise a first ligand having affinity for the first analyte, and a series of second reaction sites each comprising different known concentrations of an immobilised second analyte;
(ii) removing any unbound first analyte;
(iii) contacting the device with a second ligand that is detectably labelled and which has affinity for the first analyte, and a third ligand that is detectably labelled and which has affinity for the second analyte;
(iv) removing any unbound second and third ligands; and
(v) measuring the amount of second and third ligands bound onto the support, wherein measurement of the third ligand is used to establish a calibration curve, used to determine the amount of first analyte present in the sample. The first and second analytes may be the same or different.

According to a third aspect of the invention, a method for improving the detection of the binding of a first analyte to a first ligand immobilised on a microarray device, comprises calibrating the detection by means of a series of reaction sites on the microarray device comprising different known concentrations of a second analyte.

According to a fourth aspect of the invention, a series of reaction sites are provided on a support material, the reaction sites comprising different known concentrations of an analyte, and which are used to provide internal calibration control in a binding assay.

The present invention permits a calibration control to be established for a binding assay in a simple, convenient and efficient manner. Placing the calibration control reaction on the same support as used to detect the presence of a target analyte in a biological sample, reduces the need for separate supports and allows all reactions to be initiated together.

DESCRIPTION OF THE DRAWINGS

The invention is described with reference to the accompanying drawings, where.

DESCRIPTION OF THE INVENTION

Figure 1:
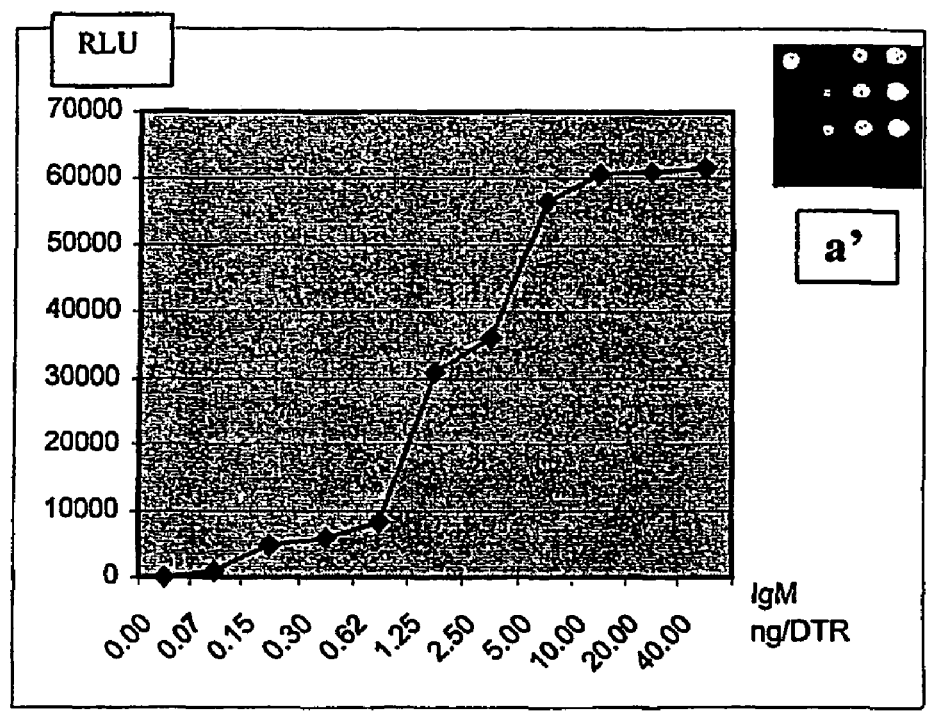
FIG. 1 is a graphic representation of the measurement of IgM present on a microarray.
Figure 1:
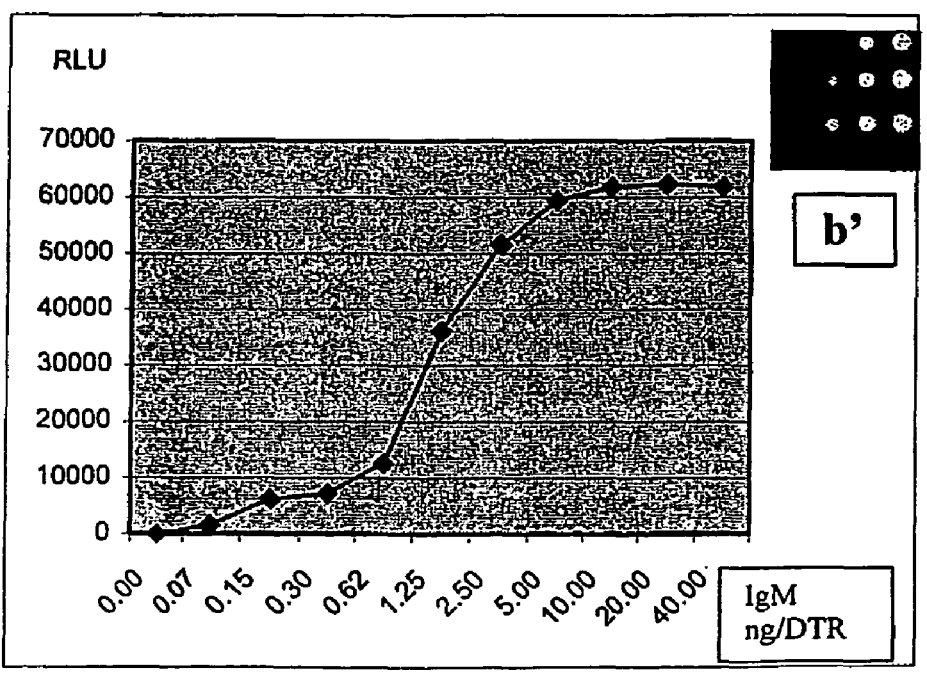

The present invention makes use of conventional microarray devices. These comprise typically a suitable support material, such as silicon, plastics, ceramics or glass, onto which discrete reaction sites are positioned, each comprising an immobilised analyte. Suitable devices are disclosed in GB-A-2324866, the content of which is incorporated herein by reference.

The support material used in the invention may be any suitable size or shape, preferably less than 2 cm$^2$, more preferably about or less than 1 cm$^2$. The discrete reaction sites may be positioned in any conventional way. Preferably, the reaction sites are separated by less than 200 µm, more preferably less than 100 µm, and most preferably 10-15 µm. The support material has preferably a flat, planar surface onto which the analytes are to be immobilised.

The analytes may be immobilised on the surface of the material using conventional means. Covalent immobilisation is preferred. Passive adsorption may also be used, but this form of immobilisation is susceptible to changes in pH, temperature and ionic strength, and may in some instances result in release of weakly-bound molecules during incubation and washing steps, thus contributing to poor reproducibility. It is of course desirable that the molecules retain maximum activity, after the immobilisation procedure.

Covalent immobilisation may be carried out using conventional techniques, typically using a chemically-reactive linker molecule, which can be activated under defined conditions. Examples of suitable linker molecules are described in GB-A-2324866.

The analyte that is to be used in the calibration system can be the same or different from that to be determined from a test sample in the assay. The analyte may be any molecule which has affinity for a particular ligand. For example, the analytes may be polynucleotides, e.g. DNA, RNA, or functional analogues thereof. Alternatively, proteins and peptides may be used, e.g. enzymes, antibodies, receptors or hormones. The molecules may also be viruses or organic compounds.

The preferred use of the devices is in immunoassays, where an antibody or antigen is the analyte. Immunoassay techniques are used widely in the art, and methods for carrying them out are apparent. In this context, the microarray will comprise a series of (second) reaction sites with known concentrations of the analyte that forms the calibration system, and a series of (first) reaction sites each comprising an immobilised ligand that has affinity for the analyte present in the target sample.

The immobilised ligand may be, for example, a particular antibody, an allergen or a specific enzyme which is targeted by the analyte in the test sample. All this will be evident to the skilled person based on conventional techniques.

The detection of the analyte in the test sample and/or that of the calibration system is carried out by the separate addition of a further ligand that is detectably labelled and which has affinity for the analyte. For example, the analyte can be the antibody IgE, and the detecting ligand can be an anti-IgE antibody that is labelled with a fluorescent label. This form of detection is the same as that used in conventional immunoassays, and so it will be apparent to the skilled person how to carry these steps out.

Suitable labels will be apparent to the skilled person, based on conventional detection systems. For example, the label may be fluorescent, chemiluminescent, colourimetric or bioluminescent.

Each device will comprise a series of discrete reaction sites that comprise different known amounts of an analyte. This is used to produce an internal calibration curve.

In this context, the concentration of analyte per reaction site necessary for use in the invention can be determined by the skilled person, depending on the nature of the analyte, etc. For the avoidance of doubt, each of the reaction sites that make up the calibration system are on the same support, and are not separated by walls or barriers that prevent the sites being in contact with the same fluid sample.

It will be apparent to the skilled person what range of analyte concentrations should be used for the calibration control. The calibration range will include typically the maximum concentration of immobilised analyte to be used in the assay. In a preferred embodiment, the concentration ranges from $2 \times 10^{-4}$ ng to 40 ng.

The internal calibration can be set up on the microarray device with as many reaction sites as required. Usually, there will be from 3 to 20 reaction sites that are utilised. Preferably, there will be from 4 to 15, and most preferably from 4 to 10.

The series of calibration reaction sites will be located at a known position on the microarray device, usually in one corner to allow easy identification.

The following Examples illustrate the invention.

EXAMPLE 1

Detection in One Biochip (Microarray) of Ascending Concentrations of Human IgM.

In this experiment, volumes of 20 nl per Discrete Test Region DTRs containing ascending concentrations of purified human IgM were applied directly to a biochip in 50 mM carbonate buffer, pH 9.5, containing 0.5M NaCl. The range of concentrations applied was 0, 0.07, 0.15, 0.30, 0.60, 1.25, 2.5, 5, 10, 20, 40 ng per DTR. The detecting agent, antihuman IgM peroxidase-labelled antibody was then added. Following a washing step with Tris buffer, Saline containing Tween 20 detergent, and chemiluminescent development, a calibration curve of human IgM was detected on the biochip. FIG. 1 illustrates Example 1. Graphical representation (a,b) and visual depiction (a',b') show the calibration (standard) curves for purified human IgM on one biochip. The designations a, a', represent a GOPS activated surface; and designations b, b', represent an ICPTES activated surface (GB-A-2324866). The graphs were obtained by plotting Relative Light Units (RLU) along the ordinate against the amount of purified IgM in ng per DTR.

EXAMPLE 2

Detection in One Biochip of Ascending Concentrations of Human IgG.

In this experiment volumes of 10 nl per DTR containing increasing concentrations of purified human IgG were applied directly to the biochip in 50 mM carbonate buffer, pH 9.5, containing 0.5M NaCl. The range of concentrations applied was 0, 0.042, 0.085, 0.17, 0.34, 0.68, 1.36, 5.46, 10.92, 21.85 ng per DTR. Addition of the detecting agent, antihuman IgG peroxidase-labelled antibody, followed by a washing step with TBST and chemiluminescent development resulted in a calibration curve for human IgG on the biochip.

Figure 2:
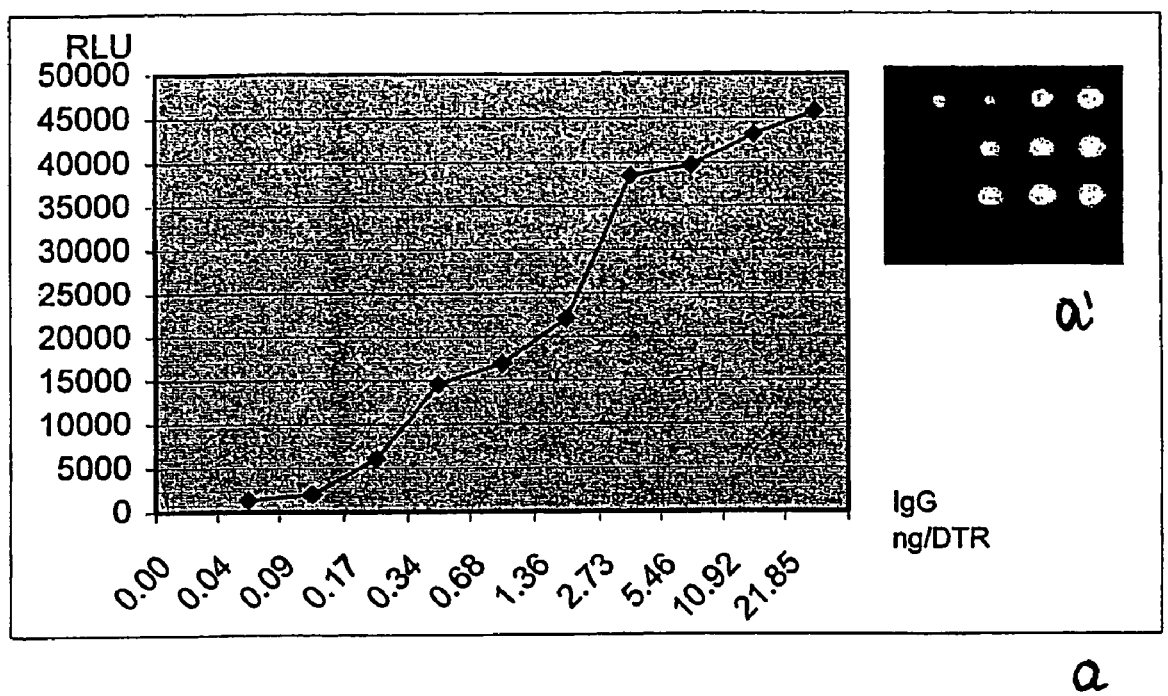
FIG. 2 is a graphic representation of the measurement of IgG present on a microarray.

FIG. 2 illustrates the results of Example 2. Graphical depiction (a) and visual depiction (a') show a calibration (standard) curve for purified human IgG on one biochip in a GOPS-activated surface.

EXAMPLE 3

Detection in One Biochip of Ascending Concentrations of Human FSH

Figure 3:
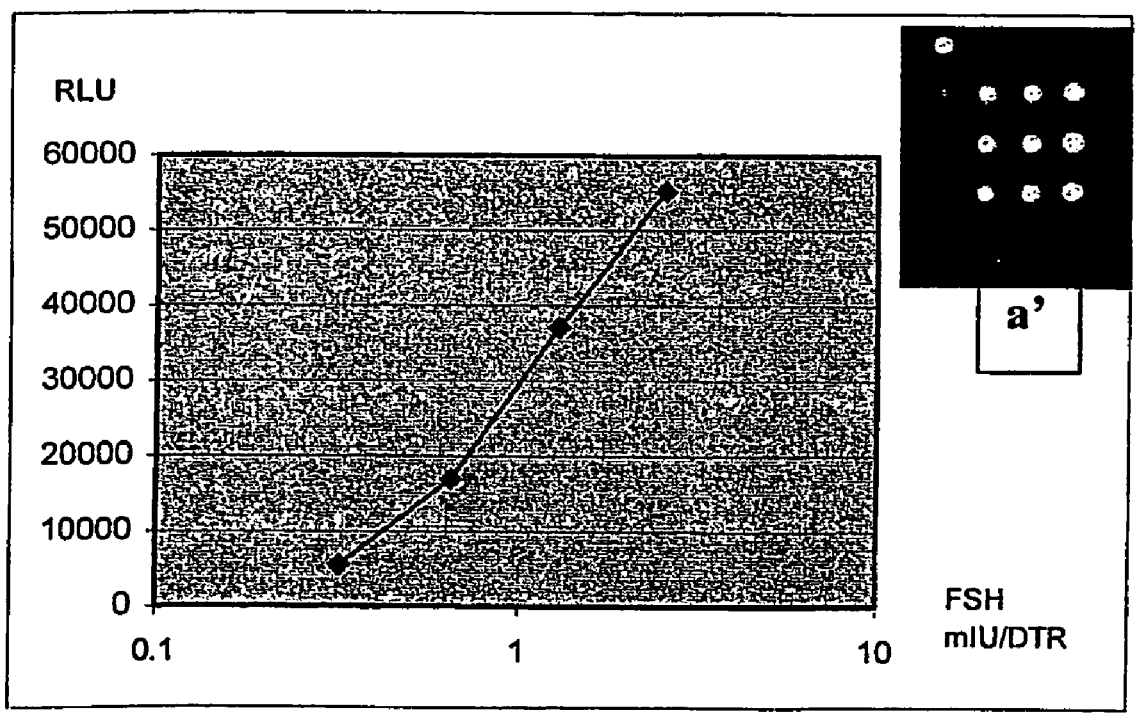
FIG. 3 is a graphic representation of the measurement of follicle stimulating hormone (FSH) present on a microarray.

In this experiment volumes of 20 nl per DTR containing increasing concentrations of human FSH were applied directly to the biochip surface in 50 mM carbonate buffer, pH 9.5, containing 0.5M NaCl. The concentration ranged from 0, 0.32, 0.64, 1.28, 2.6 mIU/DTR. After the addition of the detecting agent, antihuman FSH peroxidase-labelled antibodywas added, followed by washing with TBST and chemiluminescent development; the four ascending concentrations of the human FSH were detected simultaneously on the biochip. FIG. 3 illustrates the results of Example 3.

EXAMPLE 4

Simultaneous detection in samples of a series of highly purified human IgE calibrators, total IgEs, and specific IgEs on biochips.

In this experiment two series of reaction sites of 10 nl define the DTRs. The first series is represented by three DTRs and contains the ligands which bind specifically the analytes of interest: total IgE and specific IgEs to peanuts and a mixture of grass pollens. The second series of reaction sites is defined by six DTRs with increasing concentrations of highly purified from myeloma human IgE calibrators: 0, 50, 200, 700, 1000, 2000 IgE kU/L per DTR The ligands and the IgE calibrators were applied onto biochips in 50 mM carbonate buffer, pH 9.5.

After incubation with patient samples and washing with Tris buffer saline Tween 20 (TB ST), the detecting agent, antihuman IgE peroxidase-labelled antibody was added. After completion of the immune reaction, other washing steps were performed to remove non-bound reactants.

Chemiluminescent development allowed the simultaneous detection, visualisation, calibration and measurement of total and specific IgEs on microarrayed biochips.

Results for total IgE and specific IgEs from allergic patients were simultaneously quantified with the present device:

Sample 1: grass pollen and peanuts positive sample: total IgE: 968 $kU_A/L$, grass pollen IgE: 88 kUA/L, peanut IgE: 62 $kU_A/L$.

Sample 2: peanut positive sample: total IgE: 717.5 kU/L, grass pollen IgE: 0, peanut IgE: 99.5 $kU_A/L$ Sample 3: grass pollen positive sample: total IgE: 883 $kU_A/L$, grass pollen IgE: 128 $kU_A/L$, peanut IgE: 0.

Sample 4: tree pollen positive sample: total IgE: 415 kU/L, grass pollen IgE: 0, peanut IgE: 0.

Figure 4:
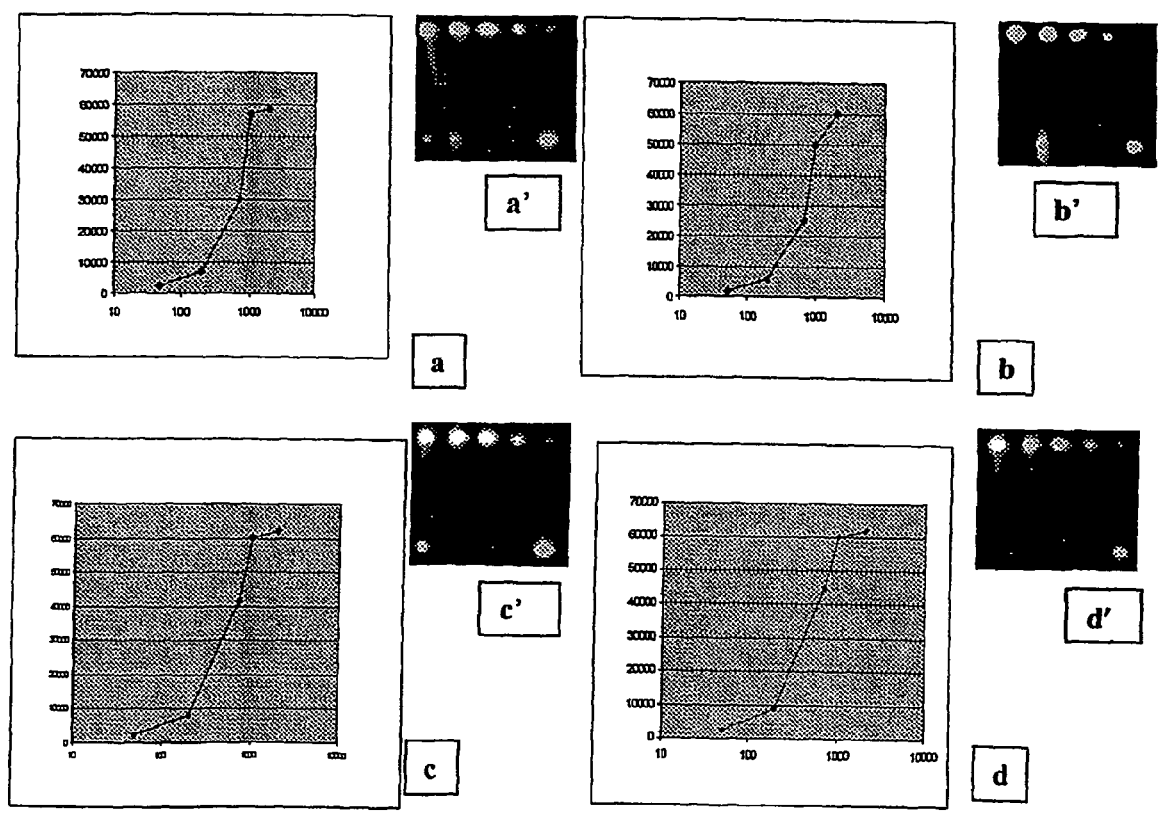
FIG. 4 shows graphic representations of the measurement of IgE for each of: grass pollen and peanut (a/a'), peanut (b/b'), grass pollen (c/c) and tree pollen (d/d'), the horizontal axis representing the concentration of IgE in kU/L per DTR, and the vertical axis representing relative light units (RLU).

FIG. 4 illustrates the results of Example 4.

The invention claimed is:

1. An assay for simultaneously measuring an amount of a first analyte and developing a calibration curve in a sample, comprising the steps of:
   (i) contacting the sample with a device that comprises:
       one or more first reaction sites which comprise an immobilized first anlayte, or a first ligand having affinity for the first analyte, under conditions that permit binding between the first ligand and the first analyte, and a series of between 3 and 20 second reaction sites each comprising a second analyte, wherein different second reaction sites comprise the second analyte at different known concentrations;
   (ii) removing any unbound first analyte;
   (iii) contacting the device with a second ligand that is detectably labeled and which has affinity for the first analyte, and a third ligand that is detectably labeled and which has affinity for the second analyte under conditions that permit binding between the first analyte and the second ligand, and between the third ligand and the second analyte;
   (iv) removing any unbound second and third ligands;
   (v) measuring an amount of the second and the third ligands bound to a support; and
   (vi) developing a calibration curve based on the measurement of the third ligand simultaneously with measuring the amount of the first analyte present in the sample.

2. An assay according to claim 1, wherein the device is a support material comprising an array of discrete first reaction sites, each reaction site comprising the immobilised first analyte, or a ligand having affinity for the first analyte, and the series of second reaction sites comprising the second analyte, of different known concentrations, are immobilised on the support.

* * * * *